United States Patent [19]

Dursch et al.

[11] 4,069,245

[45] Jan. 17, 1978

[54] PREPARATION OF PHOSPHONIC AND/OR PHOSPHINIC ACIDS

[75] Inventors: Walter Dursch, Schneidhain, Taunus; Hans-Jerg Kleiner, Kronberg, Taunus; Horst-Dieter Thamm, Kelkheim, Taunus, all of Germany

[73] Assignee: Hoechst Aktiengesellschaft, Frankfurt am Main, Germany

[21] Appl. No.: 609,093

[22] Filed: Aug. 29, 1975

[30] Foreign Application Priority Data

Aug. 31, 1974 Germany .............................. 2441878

[51] Int. Cl.$^2$ ........................... C07F 9/30; C07F 9/38; C07C 27/00
[52] U.S. Cl. ...................... 260/502.4 R; 260/502.4 P; 260/632 R
[58] Field of Search .................. 260/502.4 R, 502.4 P, 260/632 R

[56] References Cited

U.S. PATENT DOCUMENTS

| | | | |
|---|---|---|---|
| 2,776,985 | 1/1957 | McKinnis ...................... 260/502.4 R |
| 3,184,496 | 5/1965 | Baranauckas et al. ........ 260/502.4 R |
| 3,202,692 | 8/1965 | Weil et al. ...................... 260/502.4 R |
| 3,666,838 | 5/1972 | Kollenitsch et al. ......... 260/502.4 R |

OTHER PUBLICATIONS

Canavan et al., "J. Chem. Soc." (London) Jan. 1962, pp. 331–334.

Primary Examiner—Joseph E. Evans
Attorney, Agent, or Firm—Curtis, Morris & Safford

[57] ABSTRACT

Preparation of phosphonic and/or phosphinic acids by hydrolytic cleavage of phosphonic and/or phosphinic acid alkyl esters in the presence of the phosphonic and/or phosphinic acid by carrying out the hydrolysis at a temperature of from 160° to 250° C with the use of at least a stoichiometric amount of water, and by distilling off the alkanol formed, optionally together with water.

14 Claims, No Drawings

PREPARATION OF PHOSPHONIC AND/OR PHOSPHINIC ACIDS

The present invention relates to a process for the preparation of phosphonic and phosphinic acids.

The processes hitherto known for the preparation of phosphonic or phosphinic acids from the corresponding alkyl esters easily obtainable are generally carried out using mineral acids or hydrogen halides. They have many disadvantages; thus, they require special methods for the purification of the final product to liberate it from the mineral acids used, or they cause the formation of considerable amounts of by-products.

Another process is known according to which phosphonic or phosphinic acid alkyl esters, in the presence of the corresponding phosphonic or phosphinic acids, are subjected to a hydrolytic splitting at temperatures of from 90° to 150° C. The reaction temperatures are expressly limited to a maximum of 150° C, preferably 140° C, since only up to these temperatures decomposition and discoloration of the products are avoided. However, this process so far has not been applied on an industrial scale since the necessary reaction times are too long.

Surprisingly, there has now been found a process for the preparation of phosphonic and/or phosphinic acids by saponification of the corresponding phosphonic and/or phosphinic acid alkyl esters, which process overcomes the disadvantages of the known processes and gives phosphonic and/or phosphinic acids of excellent quality with practically quantitative yields.

Subject of the present invention is therefore a process for the preparation of phosphonic and/or phosphinic acids of the formula (I)

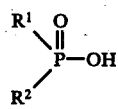
(I)

were $R^1$ is an alkyl radical having from 1 to 20 carbon atoms, an alkenyl radical having from 2 to 20 carbon atoms, an aralkyl radical having from 7 to 12 carbon atoms or an aryl radical having from 6 to 10 carbon atoms, these radicals optionally being mono- to trisubstituted, preferably monosubstituted, by Cl, Br, alkyl or alkoxy groups each having from 1 to 4 carbon atoms; or $R^1$ is a radical of the formula (Ia)

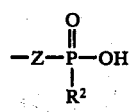
(Ia)

where Z is an alkylene radical having from 2 to 6 carbon atoms, a phenylene, biphenylene, naphthylene radical or a radical or the formula (Ib)

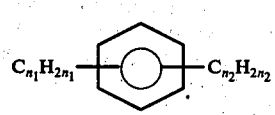
(Ib)

where $n_1$ and $n_2$ are identical or different integers of from 1 to 4, preferably $n_1 = n_2 = 1$; and $F^2$ in the formulae (I) and (Ia) is either as defined for $R^1$, except the radical of formula (Ia), $R^1$ and $R^2$ being either identical or different, by hydrolytic cleavage of phosphonic and/or phosphinic acid or OH; by hydrolytic cleavage of phosphonic and/or phosphinic acid alkyl esters of the formula (II)

(II)

where $R^3$ is as defined above for $R^1$ except the radical of formula (Ia), or a radical of the formula (IIa)

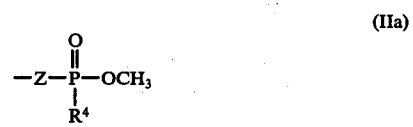
(IIa)

where Z is as defined in formula (Ia), and $R^4$ in formulae (II) and (IIa) is either as defined for $R^3$ except the radical of formula (IIa), $R^3$ and $R^4$ being either identical or different, or $OCH_3$ or OH; in the presence of the phosphonic and/or phosphinic acid of formula (I), which comprises carrying out the hydrolysis at a temperature of from 160° to 250° C, preferably from 170° to 190° C, with the use of at least a stoichiometric amount of water, and by distilling off the alkanol formed, optionally together with water.

The process of the invention is generally carried out as follows: the ester of formula (II) and from 2 to 30 weight %, preferably from 5 to 20 weight %, relative to the ester, of the corresponding acid of formula (I) are heated to the desired reaction temperature, and then the water is added in such a manner that the reaction temperature is maintained. A good intermixing of the reactants is recommended.

Of course, the reaction mixture and the water may be heated simultaneously to reaction temperature with water optionally distilling off, and the water still required after having attained the reaction temperature may be added as indicated above. It is also possible to heat the ester of formula (II) alone to reaction temperature and to add subsequently water or an aqueous solution of the acid of formula (I), provided that a certain induction time is taken into consideration which is due to the fact that the amount of catalytically active acid of formula (I) necessary for a rapid course of the reaction is formed only then. Especially in the case where water alone is added, the catalytically active amount of acid of formula (I) is formed by hydrolysis from the ester of formula (II) before the beginning of the reaction. The upper limit of the acid/ester ratio is set only by economic considerations; anyhow it rises toward infinity with the hydrolysis proceeding.

According to the process of the invention, the methanol formed in the reaction is distilled off, and advantageously separated in usual manner via a distillation column or an equivalent device from the entrained water which may be recycled into the hydrolysis.

As stoichiometric amount, there is required 1 mol of water for each ester group of the compound of formula (II). Generally, however, it is advantageous to use an excess of water, which depends above all on the efficiency of the device used for separating the methanol.

On the average, in the case of industrial equipment, a water excess of from 10 to 50%, above the stoichiometric amount is used. In order to accelerate the hydrolysis and to complete it more rapidly, it may be advantageous to add large amounts of water towards the end of the hydrolysis, so that the excess may amount up to 100%. The methanol containing water obtained may be reused for a further hydrolysis. Water excesses of more than 100%, for example up to 200% or more may be used without adversely affecting the process, but they are disadvantageous because the alkanol contained in the excess water, for reasons of preventing pollution, would have to be eliminated by distillation.

The pressure to be chosen for the process of the invention is not critical, but the process is preferably carried out under atmospheric pressure. However, any other pressure, especially elevated pressure, may also be applied, preferably a pressure below the vapor pressure of the water and/or the methanol at reaction temperature.

By adding a quantity of water below the stoichiometric amount, it is possible to attain a partial hydrolysis only, so that mixtures of esters, semi-esters and/or acids are obtained.

The process may be carried out batchwise or continuously.

The reaction temperatures are from 160° to 250° C, preferably from 170° to 190° C; the reaction temperatures required rising towards the upper limit of the intervals with increasing number of carbon atoms in the radicals $R^1$ or $R^2$.

Of course, the hydrolysis of the esters of formula (II) according to the process of the invention may be carried out also in the presence of other acidic catalysts, for example sulfuric or p-toluenesulfonic acid. However, an especially advantageous embodiment of the process of the invention is based on avoiding the use of catalysts foreign to the system, thus allowing the obtention of the desired final products in pure form and practically free from water. Contrary to the teaching of the state of the art, at the elevated temperatures of the process of the invention at which the reaction mixture cannot but dissolve small amounts of water, the hydrolysis proceeds not only with considerably increased reaction speed, but also decomposition and discoloration as described in the literature are not observed. This result is very surprising, especially in the case of high molecular weight products. It is also surprising that at the reaction temperatures according to the invention practically no pyrophosphonic acids or anhydrides are formed and despite the tendency to alkylation of the methyl esters used dimethyl ethers are formed only in insignificant amounts.

As starting products of formula (II), phosphonic acid dimethyl or monoethyl esters, phosphinic acid methyl esters and the different biphosphonic and biphosphinic acid methyl esters are used, such as the dimethyl esters of ethanephosphonic acid, propanephosphonic acid, hexanephosphonic acid, octanephosphonic acid, hexadecanephosphonic acid, chloromethanephosphonic acid, p-bromobenzenephosphonic acid, the methyl esters of octanephosphonic acid, methylethylphosphinic acid, methyloctylphosphinic acid, methylvinylphosphinic acid, the dimethyl esters of ethane-1,2-bis-methylphosphinic acid, phenylene- 1,4-bis-methylphosphinic acid, benzylphosphonic acid, methylbenzylphosphinic acid methyl ester, eicosanephosphonic acid dimethyl ester, the methyl esters of methyleicosylphosphinic or methylphenylphosphinic acid.

Mixtures of the corresponding mono- and dialkyl esters may also be used.

Preferred radicals $R^1$ or $R^2$ which according to formula (I) are linked to the phosphorus via a direct C — P bond are those containing from 1 to 16, especially from 4 to 12 carbon atoms.

It is recommended to carry out the hydrolysis, especially at the beginning of the reaction, in an inert gas atmosphere. As inert gases, there may be used for example nitrogen or argon or $CO_2$. The reaction may also be carried out in the presence of a high-boiling inert solvent such as o-dichlorobenzene, dichlorotoluene, mono- or dichloroxylene.

After complete reaction, the phosphonic and phosphinic acids obtained as crude products may be purified according to known methods; phosphonic acids may for example be recrystallized, phosphinic acids distilled.

Phosphonic and phosphinic acids are interesting intermediate products, for example for the preparation of plant protection products. Furthermore, they may be used, optionally also in the form of their salts, as textile auxiliaries, antistatic or flame retarding agents, soluted, anti-corrosion or flotation auxiliaires.

The following examples illustrate the invention.

EXAMPLE 1

154 g of chloromethanephosphonic acid dimethyl ester and 15.4 g of chloromethanephosphonic acid are heated to 165° – 170° C. Subsequently, with thorough agitation, a total of 70 ml of water is added dropwise within 4 hours. Methanol and water are distilled off via a distillation column. In a subsequent cooling trap, 11 g of dimethyl ether are collected, which amount corresponds to about 25 mol %, relative to the methanol amount theoretically obtained in the hydrolysis. The residue is 142.5 g of chloromethanephosphonic acid, corresponding to a yield of 100% of the theoretical yield.

EXAMPLE 2

224 g of hexadecanephosphonic acid dimethyl ester and 22.5 g of hexadecanephosphonic acid are heated to 190° – 200° C under a nitrogen atmosphere. Subsequently, with vigorous agitation, a total of 80 ml of water is added dropwise within 5 hours. A methanol/water mixture is distilled off via a distillation column, which mixture contains 38 g of methanol (90% of the theoretical amount). In a subsequent cooling trap, a small amount of dimethyl ether is collected. The residue is 227.5 g of hexadecanephosphonic acid, solidification point about 85° C, which corresponds to a 100% yield.

EXAMPLE 3

300 g of octanephosphonic acid dimethyl ester and 30 g of octanephosphonic acid are heated to 180° – 190° C under a nitrogen atmosphere. Subsequently, with vigorous agitation, 60 ml of water are added dropwise within 2 hours. The methanol formed is distilled off via a distillation column. In a subsequent cooling trap, 3 g of dimethyl ether are collected, which corresponds to about 5 mol %, relative to the methanol amount theoretically obtained in the hydrolysis. The residue is 292 g of octanephosphonic acid, solidification point 81° C, which corresponds to a yield of 100%.

When the same reaction is carried out at 200° C, the reaction time is 1.5 hours.

EXAMPLE 4

65 g of benzenephosphonic acid dimethyl ester and 6.5 g of benzenephosphonic acid are heated to 180° C. Subsequently, with vigorous agitation, 13 ml of water are added dropwise within 5 hours. The methanol formed in the reaction is distilled off via a distillation column. In a subsequent cooling trap, 3.3 g of dimethyl ether are collected, which corresponds to about 20 mol %, relative to the methanol amount theoretically obtained in the hydrolysis. The residue crystallizes and is 61.6 g of benzenephosphonic acid, melting point 158° – 160° C, which corresponds to a yield of 100%.

EXAMPLE 5

61 g of methylethylphosphinic acid methyl ester and 6.1 g of methylethylphosphinic acid are heated to 180° C. Subsequently, with vigorous agitation, 10 ml of water are added dropwise within 6.5 hours. The methanol formed in the reaction is distilled off via a column. In a subsequent cooling trap, 1 g of dimethyl ether is collected, which corresponds to about 9 mol %, relative to the methanol amount theoretically obtained in the hydrolysis. The residue is 60 g of methyethylphosphinic acid (boiling point at 0.7 mm HG: 130 – 132° C), which corresponds to a yield of 100%.

EXAMPLE 6

26.2 g of phenylene-1,4-bis-methylphosphinic acid methyl ester, 2.6 g of phenylene-1,4-bis-methylphosphinic acid and 10 ml of o-dichlorobenzene are heated to 180° C.. Subsequently, with vigorous agitation, 4 ml of water are added dropwise within 6 hours. The methanol formed in the reaction is distilled off via a column. In a subsequent cooling trap, a very small amount of dimethyl ether is collected. Subsequently, the dichlorobenzene is distilled off in a water-jet vacuum. 26 g of phenylene-1,4-bis-methylphosphinic acid, melting point 230° C, are obtained, which corresponds to a 100% yield.

EXAMPLE 7

276 g of ethanephosphonic acid dimethyl ester are heated to 180° C. Subsequently, with vigorous agitation, 80 ml of water are added dropwise within 10 hours. The methanol formed in the reaction is distilled off over a distillation column. In a subsequent cooling trap, some dimethyl ether is collected. The residue is 220 g of ethanephosphonic acid, which corresponds to a yield of 100%.

We claim:

1. A process for the preparation of methyl alcohol and phosphonic and/or phosphinic acids of the formula (I)

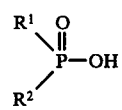

where $R^1$ is an alkyl radical having from 1 to 20 carbon atoms, an alkenyl radical having from 2 to 20 carbon atoms, an aralkyl radical having from 7 to 12 carbon atoms or an aryl radical having from 6 to 10 carbon atoms, these radicals optionally being mono- to trisubstituted by Cl, Br, alkyl or alkoxy groups each having from 1 to 4 carbon atoms; or $R^1$ is a radical of the formula (Ia)

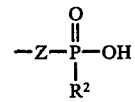

where Z is an alkylene radical having from 2 to 6 carbon atoms, a phenylene, biphenylene, naphthylene radical or a radical of the formula (Ib)

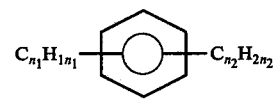

where $n_1$ and $n_2$ are identical or different integers of from 1 to 4, and $R^2$ in the formulae (I) and (Ia) is either as defined for $R^1$, except the radical of formula (Ia), $R^1$ and $R^2$ being either identical or different, or OH; by hydrolytic cleavage of phosphonic and/or phosphinic acid alkyl esters of the formula (II)

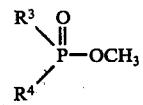

where $R^3$ is as defined above for $R^1$ except the radical of formula (Ia), or a radical of the formula (IIa)

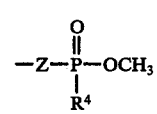

where Z is as defined in formula (Ia), and $R^4$ in formulae (II) and (IIa) is either as defined for $R^3$ except the radical of formula (IIa), $R^3$ and $R^4$ being either identical or different, or $OCH_3$ or OH; in the presence of the phosphonic and/or phosphinic acid of formula (I), which comprises carrying out the hydrolysis at atmospheric pressure and at a temperature of from 160 to 250° C, with the use of at least a stoichiometric amount of water, and by distilling off the methyl alcohol formed, optionally together with water.

2. The process as claimed in claim 1, which comprises using the ester of formula (II) together with 2 to 30 weight % of the corresponding acid of formula (I), relative to the ester of formula (II).

3. The process as claimed in claim 1, which comprises using an excess of water of up to 100%, relative to the stoichiometric amount required.

4. The process as claimed in claim 1, which comprises carrying out the reaction under an inert gas atmosphere.

5. The process as claimed in claim 1, which comprises hydrolytically producing at first the phosphonic or phosphinic acid of formula (I) required as catalyst in situ at reaction temperature from the ester of formula (II) by adding water, and continuing the hydrolysis according to the invention.

6. A process for the preparation of methyl alcohol and a phosphonic acid of the formula III

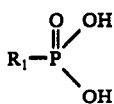

wherein R₁ is a member selected from the group consisting of ethyl, propyl, hexyl, octyl, hexadecane, chloromethyl, benzyl, p-bromobenzene and eicosyl,
or phosphinic acids of the formula V

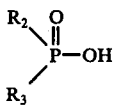

wherein R₂ is methyl and R₃ is a member selected from the group consisting of ethyl, vinyl, octyl, phenyl, benzyl and eicosyl;
by a hydrolytic cleavage reaction of a phosphonic acid ester of the formula IV

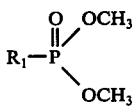

wherein R₁ is as defined above and one of said —OCH₃ can be —OH,
or by a hydrolytic cleavage reaction of a phosphinic acid ester of the formula

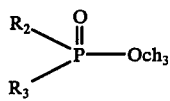

wherein R₂ and R₃ are as defined above;
wherein the hydrolytic cleavage is carried out in the presence of 2 to 30 weight % of the respective phosphonic or phosphinic acid of formula III or V, based on weight of the corresponding phosphonic or phosphinic acid ester of formula IV or VI, respectively, to form the corresponding phosphonic acid and methyl alcohol or phosphinic acid and methyl alcohol, said reaction being carried out with at least a stoichiometric amount of water being present during the reaction or being gradually added during the reaction, and said reaction being carried out at atmospheric pressure and at a temperature of 160 to 250° C, distilling off the methyl alcohol during the reaction, or distilling the methyl alcohol and water during the reaction.

7. The process of claim 1 wherein the phosphonic acid is chloromethane phosphonic acid and the phosphonic acid ester is chloromethane phosphonic acid dimethyl ester.

8. The process of claim 1 wherein the phosphonic acid is hexadecane phosphonic acid and the phosphonic acid ester is hexadecane phosphonic acid dimethyl ester.

9. The process of claim 1 wherein the phosphonic acid is octane phosphonic acid and the phosphonic acid ester is octane phosphonic acid dimethyl ester.

10. The process of claim 1 wherein the phosphonic acid is benzene phosphonic acid and the phosphonic acid ester is benzene phosphonic acid dimethyl ester.

11. The process of claim 1 wherein the phosphinic acid is methylethyl phosphinic acid and the phosphinic acid ester is methylethyl phosphinic acid methyl ester.

12. The process of claim 1 wherein the phosphinic acid is phenylene-1,4-bis-methyl phosphinic acid and the phosphinic acid ester is phenylene-1,4-bis-methyl phosphinic acid methyl ester.

13. A process for the preparation of methyl alcohol and a phosphonic acid of the formula III

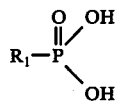

wherein R₁ is a member selected from the group consisting of ethyl, propyl, hexyl, octyl, hexadecane, chloromethyl, benzyl, p-bromobenzene and eicosyl;
by a hydrolytic cleavage reaction of a phosphonic acid ester of the formula IV

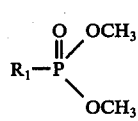

wherein R₁ is as defined above and one of said —OCH₃ can be —OH;
wherein the hydrolytic cleavage is carried out in the presence of 2 to 30 weight % of the phosphonic acid of formula III, based on weight of the corresponding phosphonic acid ester of formula IV, to form the corresponding phosphonic acid and methyl alcohol, said process consisting essentially of carrying out the reaction at atmospheric pressure and a temperature of about 160° to 250° C, while gradually adding during the reaction at least a stoichiometric amount of water sufficient to form said methyl alcohol and distilling off the methyl alcohol formed during the reaction.

14. A process for the preparation of methy alcohol and a phosphinic acid of the formula V

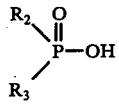

wherein R₂ is methyl and R₃ is a member selected from the group consisting of ethyl, vinyl, octyl, phenyl, benzyl and eicosyl;
by a hydrolytic cleavage reaction of a phosphinic acid ester of the formula

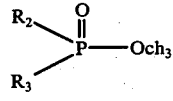

wherein R₂ and R₃ are as defined above:
wherein the hydrolytic cleavage is carried out in the presence of 2 to 30 weight % of the phosphinic acid of the formula V, based on weight of the corresponding phosphinic acid ester of formula VI, to form the corresponding phosphinic acid and methyl alcohol, said process consisting essentially of carrying out the reaction at atmospheric pressure and at a temperature of about 160 to 250° C, while gradually adding during the reaction at least a stoichiometric amount of water sufficient to form said methyl alcohol and distilling off the methyl alcohol formed.

* * * * *